United States Patent [19]

Krüger et al.

[11] Patent Number: 4,973,583
[45] Date of Patent: Nov. 27, 1990

[54] PESTICIDAL O-HALOGENOCYCLOBUTYL S-ALKYL (DI)THIPHOSPH)(ON)ATES

[75] Inventors: Bernd-Wieland Krüger, Bergisch Gladbach; Dietmar Bielefeldt, Ratingen-Hoesel; Karl-Rudolf Gassen, Odenthal; Bernhard Homeyer, Leverkusen; Benedikt Becker, Mettmann; Hans-Detlef Matthaei, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 359,618

[22] Filed: Jun. 1, 1989

[30] Foreign Application Priority Data

Jun. 9, 1988 [DE] Fed. Rep. of Germany ....... 3819632

[51] Int. Cl.$^5$ .................. C07F 9/177; C07F 9/40; A01N 57/04
[52] U.S. Cl. ................... 514/141; 514/143; 549/427; 549/497; 558/204
[58] Field of Search ............ 558/204; 514/141, 143; 549/427, 497

[56] References Cited

PUBLICATIONS

Knunyants et al., "Chem. Abst.", vol. 66, (1967), No. 94647d.

Primary Examiner—Mukund J. Shah
Assistant Examiner—E. C. Ward
Attorney, Agent, or Firm—Sprung Horn Kramer & Woods

[57] ABSTRACT

Pesticidal O-halogenocyclobutyl S-alkyl (di) thiophosph(on)ates of the formula

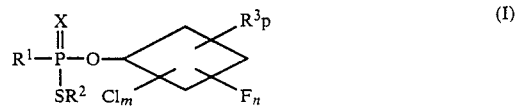

in which
x represents oxygen or sulphur,
p represents zero, one or two,
m represents zero, one or two,
n represents 2, 3 or 4
$R^1$ represents alkyl, alkoxy which is optionally interrupted by oxygen or sulphur and can be substituted by halogen, or alkenyloxy, alkinyloxy, heterocyclyl-alkoxy or cycloalkoxy which is optionally substituted by alkyl and/or halogen,
$R^2$ represents alkyl which is optionally interrupted by oxygen or sulphur and can be substituted by halogen, or alkenyl, alkinyl or heterocyclyl-alkyl and
$R^3$ represents hydrogen or alkyl.

13 Claims, No Drawings

PESTICIDAL O-HALOGENOCYCLOBUTYL S-ALKYL (DI)THIPHOSPH)(ON)ATES

The invention relates to new O-halogenocyclobutyl S-alkyl (di)thiophosph(on)ates, to several processes for their preparation and to their use as pest-combating agents, in particular as insecticides, acaricides and nematocides.

It is already known that certain O-(2,2,2-trihalogenoethyl) S-(alkyl) (di)thiophosphates, such as, for example, O-(ethyl) O-(2,2,2-trichloroethyl) S-(n-propyl) thiophosphate and O-(ethyl) O-(2,2,2-trifluoroethyl) S-(n-propyl) dithiophosphate can be used for combating pests (see DE-OS (German Published Specification) No. 2,732,930).

However, particularly at low concentrations of active compound and application rates, the insecticidal, acaricidal and nematocidal action of the known compounds is not always satisfactory.

New O-halogenocyclobutyl S-(alkyl) (di)thiophosph(on)ates of the formula (I)

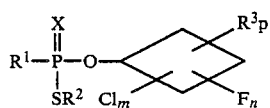

(I)

in which
x represents oxygen or sulphur,
p represents zero, one or two,
m represents zero, one or two,
n represents 2, 3 or 4,
$R^1$ represents alkyl, alkoxy which is optionally interrupted by oxygen or sulphur and can be substituted by halogen, or alkenyloxy, alkinyloxy, heterocyclyl-alkoxy or cycloalkoxy which is optionally substituted by alkyl and/or halogen,
$R^2$ represents alkyl which is optionally interrupted by oxygen or sulphur and can be substituted by halogen, or alkenyl, alkinyl or heterocyclyl-alkyl and
$R^3$ represents hydrogen or alkyl, have now been found.

It has also been found that the new O-halogenocyclobutyl S-alkyl (di)thiophosph(on)ates of the formula (I) are obtained if (a) thiophos(on)ic or dithiophos(on)ic esters of the formula (II)

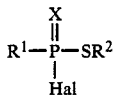

(II)

in which
$R^1$, $R^2$ and X have the meanings indicated above and
Hal represents halogen, are reacted, if appropriate in the presence of diluents and if appropriate in the presence of bases, with cyclobutanol derivatives of the formula (III)

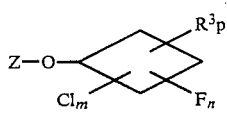

(III)

in which $R^3$, n, m and p have the meanings indicated above and
Z represents hydrogen or an equivalent of an alkali metal ion, or if (b) thiophosphoric or dithiophosphoric acid esters of the formula (I) are obtained in a first reaction stage by reacting, if appropriate in the presence of solvents and if appropriate in the presence of bases, acid halides of the formula (IV)

(IV)

in which
X, $R^2$ and Hal have the meanings indicated above, with compounds of the formula

(V)

in which
$R^4$ represents the radicals listed under $R^1$, excepting alkyl, and then reacting, in a subsequent reaction stage, if appropriate in the presence of diluents and if appropriate in the presence of bases, with cyclobutanol derivatives of the formula (III)

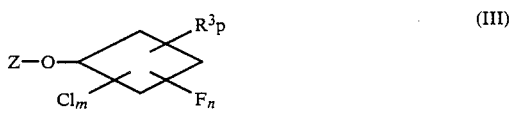

(III)

in which
Z, $R^3$, m, n and p have the meanings indicated above,
or if (c) to produce thiophosphoric or dithiophosphoric acid esters of the formula (I), in a first reaction stage the acid halides of the formula (VI)

(VI)

in which
X, $R^1$ and Hal have the meanings indicated above, are reacted with cyclobutanol derivatives of the formula (III)

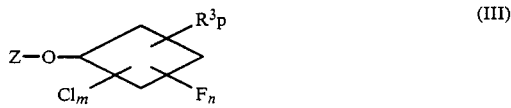

(III)

in which
Z, $R^3$, n, m and p have the meanings indicated above, if appropriate in the presence of diluents and if appropriate in the presence of bases, and in a second reaction stage the thus obtained compounds of the formula (VII)

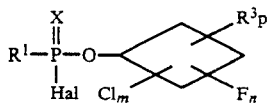 (VII)

in which
X, Hal, $R^1$, $R^3$, n, m and p have the meanings indicated above,
are reacted with compounds of the formulae (VIIIa) or (VIIIb)

 (VIIIa)

or

 (VIIIb)

in which
$Z^1$ represents an equivalent of an alkali metal ion, if appropriate in the presence of a diluent, and in a third reaction stage the thus obtained compounds of the formula (IX)

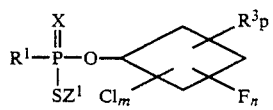 (IX)

in which
X, $Z^1$, $R^1$, $R^3$, m, n and p have the meanings indicated above,
are reacted with alkyl halides of the formula (X)

 (X)

in which
$R^2$ and Hal have the meanings indicated above, if appropriate in the presence of a diluent.

Finally, it has been found that the new O-halogenocyclobutyl S-alkyl (di)thiophosph(on)ates of the general formula (I) possess strongly marked insecticidal, acaricidal and nematocidal properties. Above all, the new compounds exhibit a very strong nematocidal action and are advantageously tolerated.

The compounds according to the invention are defined in general by the formula (I).

In the general formulae alkyl represents linear or branched alkyl having, preferably, 1 to 6, in particular 1 to 4, carbon atoms, in which connection methyl, ethyl, n-propyl, isopropyl and n-, iso-, sec.-, and t.-butyl may be mentioned as examples.

Alkyl and alkoxy which are optionally interrupted by oxygen or sulphur denote linear or branched alkoxyalkyl, alkylthioalkyl, alkoxyalkoxy and alkylthioalkoxy having, preferably, 1 to 6, in particular 1 to 4, carbon atoms per alkyl, alkoxy or alkylthio moiety.

These radicals can be substituted by one or more identical or different halogen atoms (fluorine, chlorine, bromine and iodine, preferably fluorine, chlorine and bromine).

In the general formulae, alkenyl, alkinyl, alkenyloxy and alkinyloxy are linear or branched and preferably contain 2 to 6, in particular 2 to 4, carbon atoms and, preferably, 1 double or triple bond.

Heterocyclyl-alkoxy and heterocyclyl-alkyl are linear or branched and preferably contain 1 to 4, in particular 1 or 2, carbon atoms in the alkyl or alkoxy moiety.

The heterocyclyl moiety preferably contains 5 or 6 ring members and, preferably, 1 heteroatom, oxygen being preferred as the heteroatom. The heterocyclic ring is preferably saturated. Tetrahydrofuranyl and hexahydropyranyl may be mentioned as examples of heterocyclyl moieties.

Cycloalkoxy which is optionally substituted by alkyl and/or halogen preferably contains 3 to 6, in particular 4 to 6, ring members, in which connection cyclopropoxy, cyclobutoxy, cyclopentoxy and cyclohexyloxy may be mentioned as examples. Cycloalkyloxy can be monosubstituted or polysubstituted, preferably monosubstituted to pentasubstituted, by identical or different substituents. As a substituent, alkyl is linear or branched and preferably contains 1 to 4, in particular 1 or 2, carbon atoms. As a substituent, halogen denotes fluorine, chlorine, bromine and iodine, preferably fluorine and chlorine. The 3,3,2-trifluoro-2-chlorocyclobutoxy radical may be mentioned as an example.

Hal denotes identical or different halogen, preferably chlorine, bromine and iodine, especially chlorine and bromine and particularly preferably chlorine.

m preferably represents 0 or 1 and n preferably represents 3 or 4.

The radical

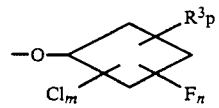

preferably represents the radical

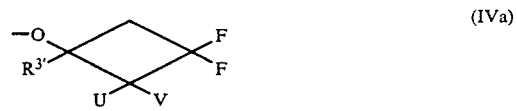 (IVa)

in which
$R^{3'}$ represents hydrogen or $(C_1-C_4)$-alkyl,
U represents hydrogen, fluorine or chlorine and
V represents hydrogen, fluorine or chlorine.

It is particularly preferable for $R^{3'}$ to represent hydrogen or methyl (preferably hydrogen), for U to represent fluorine or chlorine (preferably chlorine) and for V to represent fluorine or chlorine (preferably fluorine).

Preferred compounds, according to the invention, of the formula (I) are the compounds of the general formula (Ia)

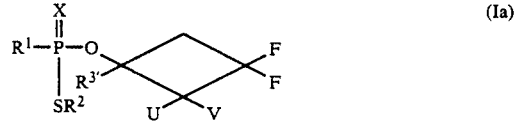 (Ia)

in which
X represents oxygen or sulphur,
$R^{3'}$ represents hydrogen or $(C_1-C_4)$-alkyl (preferably hydrogen),
U represents hydrogen, fluorine or chlorine (preferably fluorine or chlorine),
V represents hydrogen, fluorine or chlorine (preferably fluorine),
$R^1$ represents $(C_1-C_6)$-alkyl, $(C_1-C_6)$-alkoxy, $(C_2-C_6)$-alkenyloxy, $(C_2-C_6)$-alkinyloxy, 2hexahydropyranyl)methoxy, (2-tetrahydrofuranyl)methoxy, (C₁–C₆)-alkoxy-(C₁–C₄)-alkoxy, (C₁–C₆)-alkylthio-(C₁–C₄)-alkoxy or 3,3,2-trifluoro-2-chlorocyclobutoxy (preferably (C₁–C₆)-alkoxy) and R² represents (C₁–C₆)-alkyl, (C₂–C₆)-alkenyl, (C₂–C₆)-alkinyl, (2-hexahydropyranyl)-methyl, (2-tetrahydrofuranyl)-methyl, (C₁–C₆)alkylthio-(C₁–C₄)-alkyl or (C₁–C₆)alkoxy-(C₁–C₄)-alkyl (preferably (C₁–C₆)-alkyl).

Compounds of the formula (Ia) which are particularly preferred are those in which X represents oxygen or sulphur (preferably oxygen), R³' represents hydrogen or methyl (preferably hydrogen), U represents hydrogen, fluorine or chlorine (preferably fluorine or chlorine), V represents hydrogen, fluorine or chlorine (preferably fluorine), R¹ represents (C₁–C₄)-alkyl, (C₁–C₄)-alkoxy, (C₂–C₄)-alkenyloxy, (C₂–C₄)-alkinyloxy, (2-tetrahydropyranyl)methoxy, (C₁–C₄)-alkoxy-(C₁–C₄)-alkoxy or (C₁–C₄)-alkylthio-(C₁–C₄)-alkoxy (preferably (C₁–C₄)-alkoxy) and R² represents (C₁–C₄)-alkyl, (C₂–C₄)-alkenyl, (C₂–C₄)-alkinyl, (2-tetrahydrofuranyl)-methyl, (C₁–C₄)-alkoxy-(C₁–C₄)-alkyl or (C₁–C₄)-alkylthio-(C₁–C₄)-alkyl (preferably (C₁–C₄)-alkyl.

Compounds of the formula (Ia) which are very particularly preferred are those in which X represents oxygen or sulphur (preferably oxygen), R³' represents hydrogen or methyl (preferably hydrogen), U represents hydrogen, fluorine or chlorine (preferably fluorine or chlorine), V represents fluorine or chlorine (preferably fluorine), R¹ represents (C₁–C₄)-alkyl, (C₁–C₄)-alkoxy or (C₂–C₄)-alkenyloxy (preferably (C₁–C₄)-alkoxy) and R² represents (C₁–C₄)-alkyl or (C₂–C₄)-alkenyl (preferably (C₁–C₄)-alkyl).

Apart from the compounds mentioned in the preparation examples, the following O-halogenocyclobutyl S-alkyl (di)thiophosph(on)ates of the general formula (I) may be mentioned specifically:

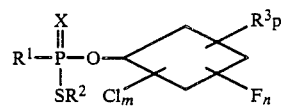

| R¹ | X | R² | (ring substituents) |
|---|---|---|---|
| CH₃ | S | CH(CH₃)C₂H₅ | F, F, F, Cl |
| C₂H₅ | S | CH(CH₃)C₂H₅ | F, F, F, Cl |
| CH₃ | S | CH(CH₃)C₂H₅ | F, F, F, F |
| C₂H₅ | S | CH(CH₃)C₂H₅ | F, F, F, F |
| CH₃ | S | CH(CH₃)C₂H₅ | CH₃, F, F, Cl, F |
| C₂H₅ | S | CH(CH₃)C₂H₅ | CH₃, F, F, Cl, F |
| CH₃ | S | C₄H₉-i | Cl, F, F, F |
| C₂H₅ | S | C₄H₉-t | Cl, F, F, F |
| CH₃ | O | C₄H₉-i | Cl, F, F, F |
| C₂H₅ | O | C₄H₉-t | Cl, F, F, F |
| CH₃O | O | C₃H₇-n | F, F, F, Cl |
| C₂H₅O | O | C₃H₇-n | F, F, F, Cl |
| C₃H₇O | O | C₃H₇-n | F, F, F, Cl |

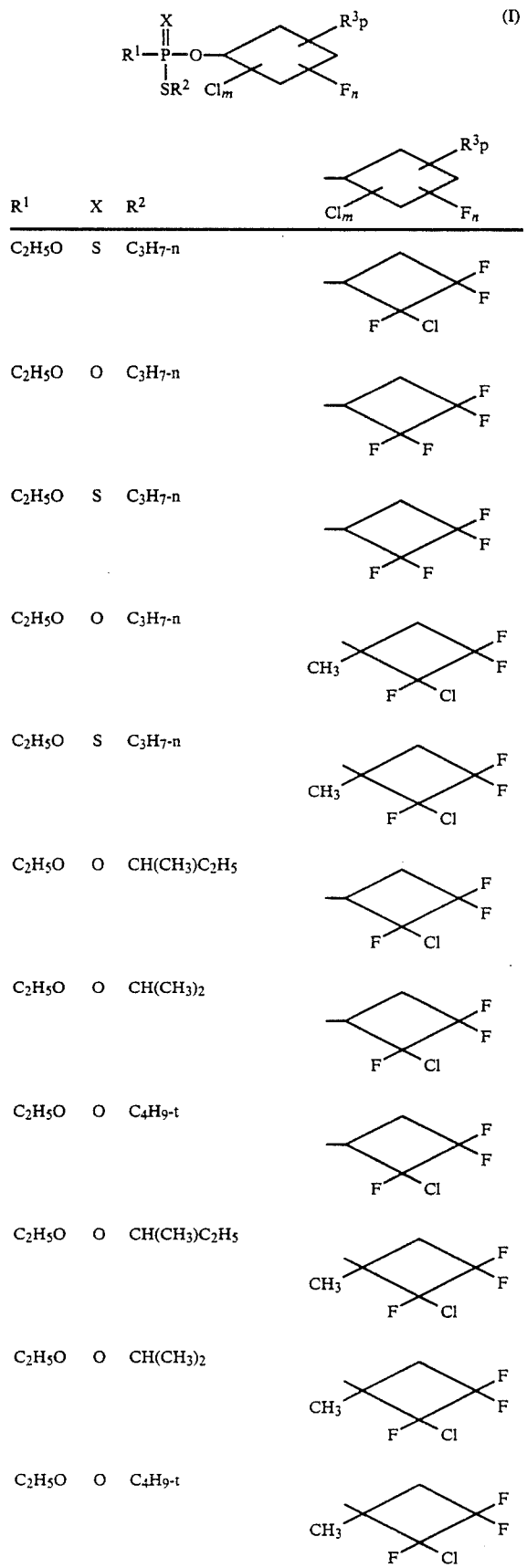
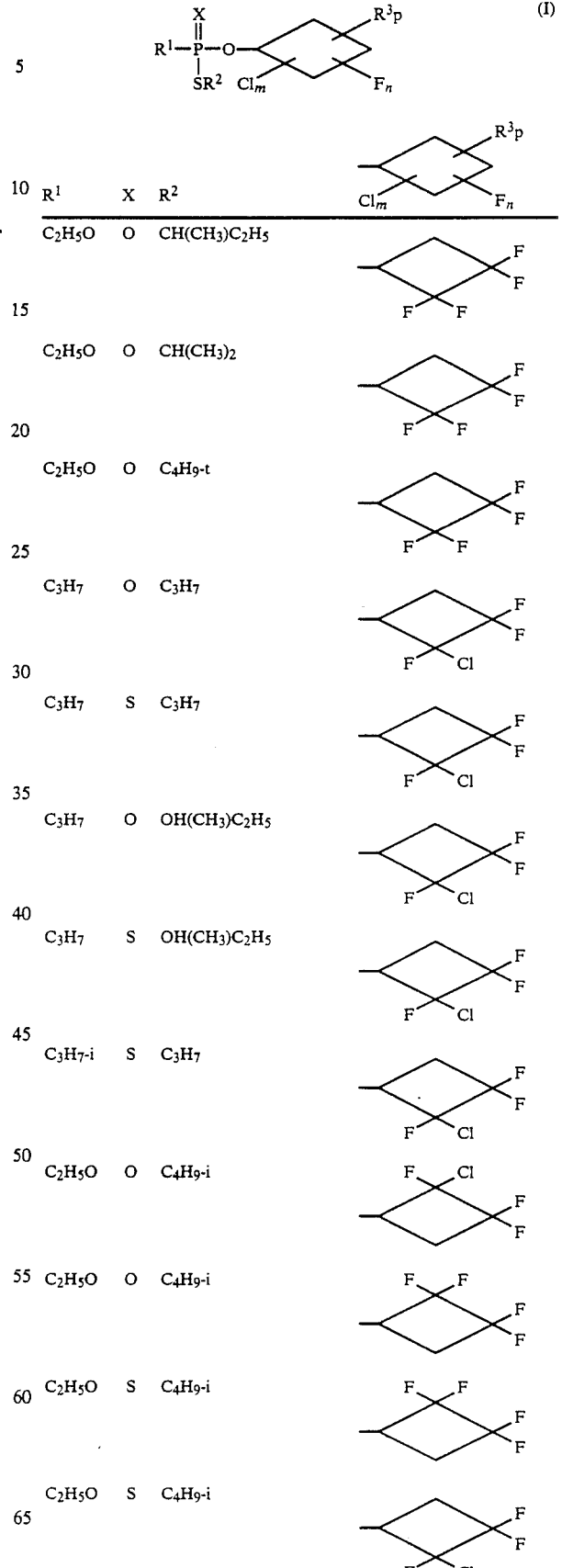

-continued $$R^1-\underset{\underset{SR^2}{|}}{\overset{\overset{X}{\|}}{P}}-O-\underset{Cl_m}{\diamond}-\underset{F_n}{\overset{R^3_p}{}} \qquad (I)$$

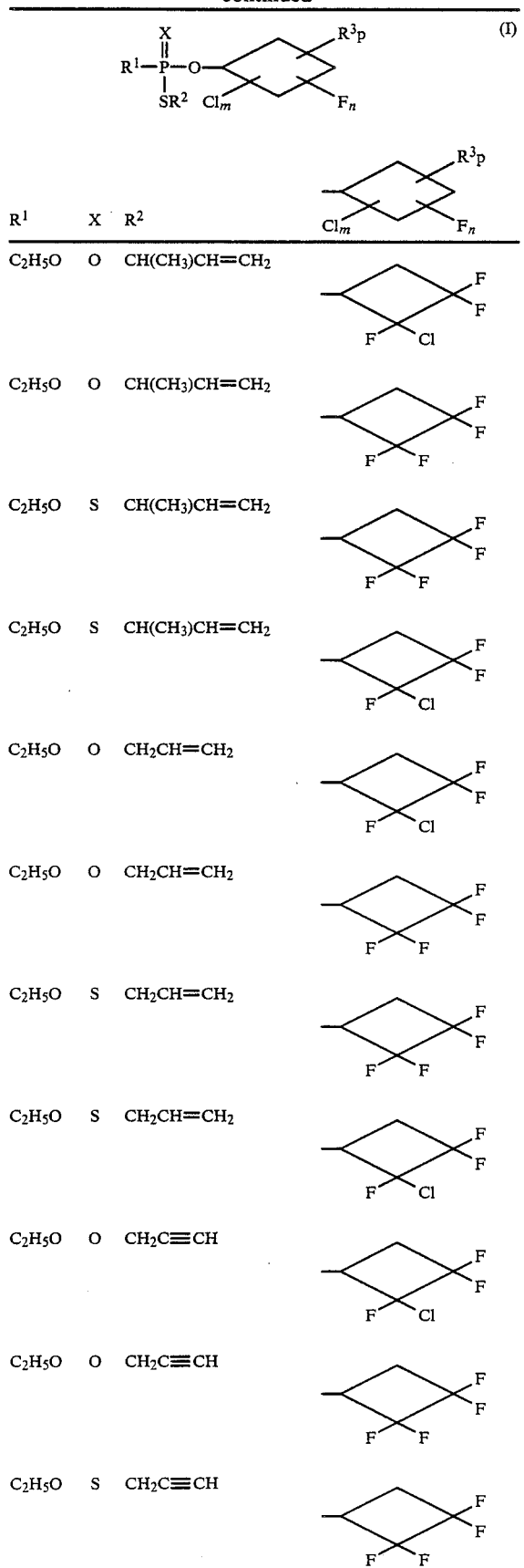

-continued $$R^1-\underset{\underset{SR^2}{|}}{\overset{\overset{X}{\|}}{P}}-O-\underset{Cl_m}{\diamond}-\underset{F_n}{\overset{R^3_p}{}} \qquad (I)$$

| $R^1$ | X | $R^2$ | ![ring] |
|---|---|---|---|
| $C_2H_5O$ | S | $CH_2C\equiv CH$ | F,F,F,Cl ring |

If, for example, O-ethyl, S-propyl chlorothiophosphate and 3,5,2-trifluoro-2-chlorocyclobutan-1-ol are used as starting materials in variant (a) of the preparation, the course of the corresponding reaction can be represented by the following equation:

$$C_2H_5O-\underset{\underset{SC_3H_7}{|}}{\overset{\overset{O}{\|}}{P}}-Cl + HO-\square(F,F,F,Cl) \xrightarrow{-HCl}$$

$$C_2H_5-\underset{\underset{SC_3H_7}{|}}{\overset{\overset{O}{\|}}{P}}-O-\square(F,F,F,Cl)$$

If, for example, S-butyl dichlorothiophosphate, methanol and 2,2,3,3-tetrafluorobutan-1-ol are used in variant (b) of the preparation, the reaction can be represented by the following equation:

1st stage:

$$n\text{-}C_4H_9S-\underset{\underset{Cl}{|}}{\overset{\overset{O}{\|}}{P}}-Cl + CH_3OH \xrightarrow{-HCl} n\text{-}C_4H_9S-\underset{\underset{OCH_3}{|}}{\overset{\overset{O}{\|}}{P}}-Cl$$

2nd stage $$n\text{-}C_4H_9S-\underset{\underset{OCH_3}{|}}{\overset{\overset{O}{\|}}{P}}-Cl + HO-\square(F,F,F,F) \xrightarrow{-HCl}$$

$$n\text{-}C_4H_9S-\underset{\underset{OCH_3}{|}}{\overset{\overset{O}{\|}}{P}}-O-\square(F,F,F,F)$$

The phosphoric or phosphoric acid derivatives of the general formulae (II), (IV) and (VI) to be used as starting materials for process variants(a), (b) and (c) are known or can be prepared by known processes (see "Methoden der organischen Chemie" ("Methods of organic chemistry") (Houben-Weyl) volume E2, 1982, Georg Thieme Verlag Stuttgart, New York, page 300 et seq and page 487 et seq).

The starting materials of formula (VII) are new and part of the present invention. They are obtained according to the first reaction stage of process variant (c). They can be isolated and purified by usual methods, e.g. by destillation or chromotography.

The cyclobutanol derivatives used as starting materials in the process according to the invention are defined by the formula (III).

The following may be mentioned as examples of the compounds of the formula (III):

3,3,2-Trifluoro-2-chlorocyclobutan-1-ol; 3,3-difluorocyclobutan-1-ol and 3,3,2-trifluoro-2-chloro-1-methylcyclobutan-1-ol and sodium, potassium and lithium salts thereof.

Amongst the compounds of the formula (III), those of the formula (IIIa)

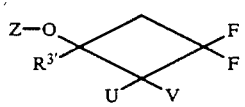
(IIIa)

are new, in which connection, in formula (IIIa),

R$^{3'}$ represents hydrogen or alkyl (preferably hydrogen),

U represents hydrogen, fluorine or chlorine (preferably chlorine),

V represents hydrogen, fluorine or chlorine (preferably fluorine), and

Z represents hydrogen or an equivalent of an alkali metal ion, subject to the proviso that U and V do not both represent fluorine.

The cyclobutanol derivatives of the formula (IIIa) are obtained by reacting alkenyl acetates of the formula (XI),

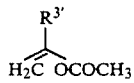
(XI)

in which

R$^{3'}$ has the meaning mentioned in formula (IIIa), with halogeno-substituted alkenes of the formula (XII)

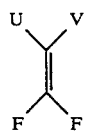
(XII)

in which

U and V have the meaning mentioned in formula (IIIa), if appropriate in the presence of solvents and if appropriate in the presence of hydroquinone and/or dipentene, and splitting off the acetyl group in a second reaction stage, for example by means of hydrazine (see also W. H. Sharkey in Fluorine Chem. Rev. Vol. 2, page 1, 1968, M. Decker, New York, and instructions for preparation).

The remaining compounds of the formula (III) can be obtained correspondingly or by known methods and processes.

The preferred definitions and ranges listed for the end products of formula (I) and/or (Ia) apply correspondingly to the starting materials in each case.

Virtually any inert organic diluents are suitable as diluents for variant (a) of the process according to the invention. These include, in particular, aliphatic and aromatic, optionally halogenated, hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobezene, ethers, such as diethyl and dibutyl ethers, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, diemthylacetamide and N-methylpyrrolidone, and also dimethyl sulphoxide, tetramethylene sulphone and hexamethylphosphoric triamide.

Variant (a) of the process according to the invention is carried out by employing 1 to 2 moles, preferably 1.0 to 1.8 moles, of cyclobutanol of the formula (III) to 1 mole of phosphorus derivative of the formula (II).

In general, the reaction is carried out in a suitable diluent. Working up is effected by customary methods. The new compounds are obtained in some cases in the form of oils which cannot, in some cases, be distilled without decomposition, but can be freed from the last volatile constituents by so-called "incipient distillation", that is to say by prolonged heating at moderately purified in this manner. The refractive index is used to characterize them.

Virtually any inert organic diluents can be used as diluents for process variants (b) and (c) of the process according to the invention. It is preferable to use the diluents mentioned in connection with the description of variant (a) of the process according to the invention.

Process variants (a), (b) and (c) can, if desired, be carried out in the presence of bases. Any customary base can be used as the base. Alkali metal carbonates and alcoholates, such as sodium carbonate, potassium carbonate, sodium methylate and ethylate and potassium methylate and ethylate, and also aliphatic, aromatic or heterocyclic amines, for example triethylamine, trimethylamine, dimethylaniline, dimethylbenzylamine, tetraethylenediamine (DABCO) and pyridine have proved particularly suitable.

In general, variants (a), (b) and (c) of the process according to the invention are carried out at temperatures between −70° C. and +110° C. The range between −40° C. and 80° C. is preferred.

In general, the reactions are carried out under normal pressure.

Variant (b) of the process according to the invention is carried out by employing 1 to 1.6 moles, preferably 1 to 1.4 moles, of the alcohol derivative of the formula (V) and 1 to 2, preferably 1 to 1.8, moles of the cyclobutanol derivative of the formula (III) to 1 mole of the compound of the formula (IV).

Variant (c) of the process according to the invention is carried out by employing of 1 to 1.6 moles, preferably 1 to 1.4 moles, of the cyclobutanol derivative of the formula (III) and 1 to 2, preferably 1 to 1.8, moles of the compounds of the formulae (VIIIa) or (VIIIb) to 1 mole of the compound of the formula (VI).

In general, the reaction is carried out in a suitable diluent and, if appropriate, in the presence of an acid acceptor. Working up is effected by customary methods.

The active compounds according to the invention are well tolerated by plants and have an advantageous toxicity to warm-blooded animals and are suitable for combating animal pests, in particular insects, arachnids and nematodes which occur in agriculture, in forests, in the protection of stores and materials and in the field of hygiene. They are effective against normally sensitive and resistant species and also against all or individual stages of development. The pests mentioned above include the following:

From the order of Isopoda, for example *Armadillidium vulgare* and *Porcellio scaber.* From the order of Diplopoda, for example, *Blaniulus guttulatus.*

From the order of Chilopoda, for example, *Geophilus carpophagus* and *Scutigera* spec. From the order of Symphyla, for example, *Scutigerella immaculata.* From the order of Thysanura, for example, *Lepisma saccharina.* From the order of Collembola, for example, *Onychiurus armatus.* From the order of Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria.* From the order of Dermaptera, for example, *Forficula auricularia.* From the order of Isoptera, for example, *Reticulitermes* spp. From the order of Anoplura, for example, *Phylloxera vastatrix, Pemphigus* spp., *Pediculus humanus corporis, Haematopinus* spp. and *Linognathus* spp. From the order of Mallophaga, for example, *Trichodectes* spp. and *Damalinea* spp. From the order of Thysanoptera, for example, *Hercinothrips femoralis* and *Thrips tabaci.* From the order of Heteroptera, for example, *Eurygaster* spp., *Dysdercus intermedius, Piesma quadrata, Cimex lectularius, Rhodnius prolixus* and *Tristoma* spp. From the order of Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp. From the order of Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica* spp., *Psyliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., Niptus hololeucus, Gibbium psylloides, Tribolium spp., *Tenebrio molitor, Agriotes* spp., *Conoderus* spp., *Melolontha melolontha, Amphimallon solstitialis* and *Costelytra zealandica.* From the order of Hymenoptera, for example, *Diprion* spp., *Hoplocampa* spp., *Lasius* spp., *Monomorium pharaonis* and *Vespa* spp. From the order of Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

From the order of Siphonaptera, for example, *Xenopsylla cheopis* and *Ceratophyllus* spp. From the order of Arachnida, for example, *Scorpio maurus* and *Latrodectus mactans.* From the order of Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp. *Tarsonemus* spp., *Bryobia praetiosa, Panonychus* app. and *Tetranychus* spp.

The phytoparasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp. and *Trichodorus* spp.

The active compounds, according to the invention, of the formula (I) are distinguished by a high insecticidal, acaricidal and, above all, nematocidal activity. They can be employed, in particular, against insects which damage plants, such as, for example, the caterpillars of the cabbage moth (*Plutella maculipennis*) or the larvae of the mustard beetle (*Phaedon cochleariae*), and also mites which damage plants, such as, for example, the red spider mite (*Tetranychus urticae*). In addition, they are excellently suitable for combating soil insects and nematodes and can be employed, for example, for combating *Phorbia antiqua* maggots or nematodes of the genus *Meloidogyne incognita.* A good root-systemic action, for example against *Phaedon cochleariae* larvae, should also be singled out. The nematocidal action of the active compounds according to the invention can also be confirmed in an in vitro test, for example against nematodes of the genus *Caenorhabditis elegans* living as endoparasites.

In addition, the active compounds, according to the invention, possess a powerful action against hygiene and pests of stored products and can be employed, for example, for combating the oriental cockroach (*Blatta orientalis*) or for combating the granary weevil (*Sitophilus granarius*). In addition, the active compounds according to the invention can be employed with particularly good results for combating pests of warm-blooded animals living as parasites (both ectoparasites and endoparasites), such as, for example, the larvae of the greenbottle fly (*Lucilia cuprina*), cattle ticks (*Boophilus microplus*), sheep scab mites (*Psoroptes ovis*), stable flies (*Stomoxys calcitrans*) or the autumn fly (*Musca autumnalis*).

In addition, the active compounds, according to the invention, of the formula (I) also possess a good fungicidal activity and can be employed for combating plant diseases, such as, for example, the pathogen of rice spot disease (*Pyricularia oryzae*) or scab and botrytis pathogens.

At appropriate application rates, the active compounds, according to the invention, of the formula (I) exhibit a herbicidal activity in addition.

Depending on their particular physical and/or chemical properties, the active compounds can be converted into customary formulations, such as solutions, emulsions, suspensions, powders, foams, pastes, granules, aerosols, natural and synthetic materials impregnated with active compound, very fine encapsulations in polymeric substance and in enveloping materials for seed, and also in formulations equipped with incendiary compositions, such as smoke cartridges, cans, spirals and the like, and also ULV cold and warm mist formulations.

These formulations are prepared in a known manner, for example by mixing the active compound with diluents, that is to say liquid solvents, liquefied gases under pressure and/or solid carriers, if appropriate using surface-active agents, that is to say emulsifiers and/or dispersing agents and/or foam-producing agents. If water is used as the diluent it is also possible, for example, to use organic solvents as auxiliary solvents. Suitable liquid solvents are, essentially: aromatic hydrocarbons, such as xylene, toluene or alkylnaphthalenes, chlorinated aromatic hydrocarbons or chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol and ethers and esters thereof, ketones, such as acetone, methyl ethyl ketone, methyl isobutyl ketone or cyclohexanone, strongly polar solvents, such as dimethylformamide and dimethyl sulphoxide, and also water; liquefied, gaseous diluents or carriers are intended to mean liquids which are gaseous at normal temperature and under normal pressure, for example aerosol propellant gases, such as halogenated hydrocarbons and also butane, propane, nitrogen and carbon dioxide; the following are examples of suitable solid carriers: natural ground materials, such as kaolins, clays, talc, chalk, quartz, attapulgite, montmorillonite or diatomaceous earth and synthetic ground minerals, such as highly disperse silica, aluminum oxide and silicates; the following are examples of suitable solid carriers for granules: crushed and fractionated natural minerals, such as calcite, marble, pumice, sepiolite and dolmite, and also synthetic granules composed of inorganic and organic powders and granules composed or organic material, such as sawdust, coconut shells, corn cobs and tobacco stalks; the following are examples of suitable emulsifiers and/or foam-producing agents: nonionic and anionic emulsifiers, such as polyoxyethylene esters of fatty acids, polyoxyethylene fatty alcohol ethers, for example alkylaryl polyglycol ethers, alkylsulphonates, alkyl sulphates and arylsulphonates, and protein hydrolysates; and the following are examples of suitable dispersing agents: ligninsulphite waste liquors and methylcellulose.

Tackifiers, such as carboxymethylcellulose or natural or synthetic, pulverulent or granular polymers or polymers in the form of latex, such as gum arabic, polyvinyl alcohol, polyvinyl acetate and natural phospholipids, such as cephalins and lecithins, and synthetic phospholipids, can be used in the formulations. Other additives can be mineral and vegetable oils.

It is possible to use colorants such as inorganic pigments, for example, iron oxide, titanium oxide and Prussian blue, and organic colorants such as alizarin, azo and metal phthalocyanine colorants and trace nutrients, such as salts of iron, manganese, boron, copper, cobalt, molybdenum and zinc.

In general, the formulations contain between 0.1 and 95 percent by weight of active compound, preferably between 0.5 and 90%.

The active compounds according to the invention can be presented in their commercially available formulations and in the use forms prepared from these formulations as a mixture with other active substances, such as insecticides, attractants, sterilants, acaricides, nematocides, fungicides, growth-regulating compounds or herbicides. Insecticides include, for example, phosphoric acid esters, carbamates, carboxylic acid esters, chlorinated hydrocarbons, phenylureas, substances prepared by means of microorganisms and others.

The active compounds according to the invention can also be present in their commercially available formulations and in the use forms prepared from these formulations as a mixture with synergists. Synergists are compounds by means of which the action of the active compound is enhanced, without the necessity for the added synergist itself to be actively effective.

The active compound content of the use forms prepared from the commercially available formulations can vary within wide ranges. The active compound concentration of the use forms can be from 0.0000001 to 95% by weight of active compound, and is preferably between 0.0001 and 1% by weight.

Use is effected in a customary manner suited to the use forms.

When used against hygiene pests and pests of stored products, the active compounds are distinguished by an excellent residual action on wood and clay and by good stability to alkali on limed substrates.

The active compounds according to the invention are also suitable for combating insects, mites, ticks and the like in the field of animal husbandry and cattle breeding, it being possible to obtain better results, for example higher milk production, higher weight, finer animal hide, longer life and the like, as a result of combating the pests.

The use of the active compounds according to the invention is effected in this field in a known manner, such as by external application in the form of, for example, dipping, spraying, pouring on and spotting on and powdering on.

The active compounds according to the invention are preferably employed as plant protection agents, in particular for combating insects and nematodes.

The preparation of the compounds according to the invention will be illustrated by means of the following examples.

PREPARATION EXAMPLES

Example 1

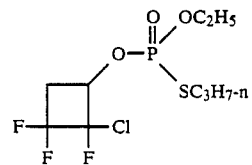

2.5 g (0.015 mol) of 3,3,2-trifluoro-2-chlorocyclobutan-1-ol are dissolved in 50 ml of tetrahydrofuran, and 6 ml of a 23% strength solution (in hexane) of n-butyllithium are added at −40° C. The mixture is stirred for 0.5 hour at 20° C. and 3.1 g (0.015 mol) of S-propyl O-ethyl chlorothiophosphorate are then added to the reaction mixture, with vigorous stirring. The mixture is stirred for 1 day at 20° C. and is then poured onto 200 ml of ice. It is then extracted with methylene chloride, the extract is dried (MgSO4) and the solvent is removed by distillation. The residue is then dissolved in a mobile phase composed of 7:3 hexane:acetone and is filtered over silica gel. Removing the solvent by distillation gives, as a residue, S-propyl O-ethyl O-(3,3,2-trifluoro-2-chlorocyclobutyl) thiophosphate.

Yield: 2.6 g (53% of theory).
$n_D^{20} = 1.4455$.

Example 2

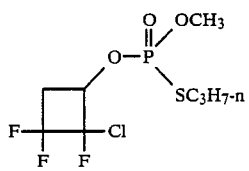

10 g (0.05 mol) of S-propyl dichlorothiophosphate are dissolved in 100 ml of toluene, and a mixture of 1.8 g (0.055 mol) of methanol and 8.5 ml (0.06 mol) of triethylamine and 10 ml of toluene is added at −5° C. The mixture is stirred for 1 hour at 0° C., and 2 g of triethylenediamine (DABCO) and 8.5 ml of triethylamine are then added to the reaction mixture. After stirring for 10 minutes at 0° C., 10.3 g (0.062 mol) of 3,3,2-trifluoro-2-chlorocyclobutan-1-ol, dissolved in 10 ml of toluene, are added dropwise slowly to the solution. The mixture is stirred for 1 hour at 20° C. and for 1 day at 50° C., and the organic phase is then extracted with water. After the toluene phase has been dried (MgSO4), the solvent is removed by distillation and the residue is filtered over silica gel, using methylene chloride as the mobile phase. This gives 4.8 g of a crude product, which is purified by distillation through a Vigreux column.

B.p.$_{0.04}$ = 93° C.
$n_D^{20} = 1.4506$
Yield: 3.3 g (21% of theory).

Example 3

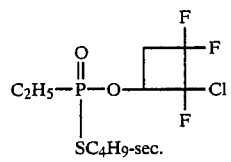

Example 3a

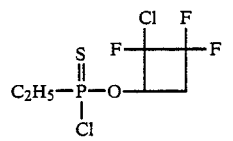

16.4 g (0.1 mol) of ethane-dichlorothiophosphonate (C2H5P(S)Cl2) are dissolved in 200 ml of tetrahydrofuran, and 16.2 g (0.1 mol) of 3,3,2-trifluoro-2-chlorocyclobutan-1-ol are added at 0° C. Then 13.5 g (0.1 mol) collidine (2,4,6-trimethylpyridine) are added dropwise slowly to the stirred solution. After stirring the solution for a day at 20° C. and an other day at 50° C. the reaction mixture is filtered over silica gel (1 kg) using methylene chloride as the mobile phase. Distillation gives 10.3 g (36% of theory) of the ethane-0-(3,3,2-trifluoro-2-chlorocyclobutyl)-chlorothiophosphonate (b.p.$_{0.03}$ = 42° C.).

Example 3b

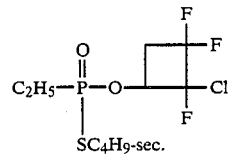

2.5 g (0.045 mol) of powdered potassium hydroxide are added to a solution of 5.8 g (0.02 mol) ethane-0-(3,3,2-trifluoro-2-chlorocyclobutyl)-chlorothiophosphonate (product of Example 3a) in acetone. The solution is stirred for 3 hours at 20° C., the solvent is distilled off and 50 ml of diethylether are added to the residue. Then the potassium salt is precipitated by the addition of hexane. This precipitation procedure is repeated. The residue is dissolved in 80 ml of acetonitrile and 3.0 g (0.022 mol) of sec.-butylbromide are added to the solution. The mixture is stirred for one day at 60° C. and methylene chloride/H2O is added. The organic phase is separated and the solvent is distilled off. The residue is then filtered over silica gel using hexane/acetone (7:3 parts by volume) as the mobile phase.

Yield: 1.2 g (18.5% of theory)
$n_D^{20} = 1.4605$

According to Example 3a also the other compounds of the formula (VII) can be obtained.

The following can be prepared analogously:

Compounds of the formula Ia

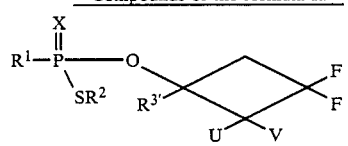

(Ia)

| Example No. | R$^1$ | R$^2$ | R$^{3'}$ | U | V | Physical data ($n_D^{20}$) |
|---|---|---|---|---|---|---|
| | | | (X = O) | | | |
| 4 | C2H5O | sec-C4H9 | CH3 | F | Cl | 1.4537 |
| 5 | C2H5O | n-C3H7 | CH3 | F | Cl | 1.4548 |
| 6 | C2H5O | sec-C4H9 | H | F | Cl | 1.4467 |
| 7 | sec-C4H9O | n-C3H7 | H | F | Cl | 1.4434 |

-continued

Compounds of the formula Ia

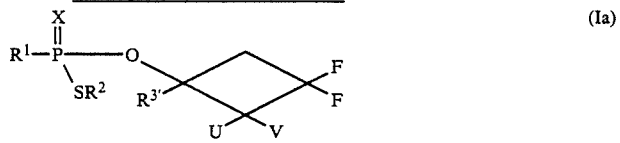

(Ia)

| Example No. | R¹ | R² | R³' | U | V | Physical data ($n_D^{20}$) |
|---|---|---|---|---|---|---|
| 8 | i-C₄H₉O | n-C₃H₇ | H | F | Cl | 1.4432 |
| 9 | C₂H₅O | CH₃ | H | F | Cl | 1.4469 |
| 10 | C₂H₅O | n-C₃H₇ | H | F | F | 1.4271 |
| 11 | CH₃OCH₂CH₂O | n-C₃H₇ | H | F | Cl | 1.4395 |
| 12 | i-C₃H₇O | n-C₃H₇ | H | F | Cl | 1.4445 |
| 13 | (tetrahydrofurfuryloxy) | n-C₃H₇ | H | F | Cl | 1.4600 |
| 14 | (tetrahydropyranylmethoxy) | n-C₃H₇ | H | F | Cl | 1.4672 |
| 15 | HC≡C—CH₂O | n-C₃H₇ | H | F | Cl | |
| 16 | CH₂=CH—CH₂CH₂O | n-C₃H₇ | H | F | Cl | 1.4576 |
| 17 | CH₂=CH—CH₂O | n-C₃H₇ | H | F | Cl | 1.4513 |
| 18 | CH₃O | sec-C₄H₉ | H | F | Cl | |
| 19 | C₂H₅O | (tetrahydrofurfuryl-CH₂) | H | F | Cl | 1.4680 |
| 20 | OCH₂CH₂Cl | n-C₃H₇ | H | F | Cl | |
| 21 | C₂H₅O | i-C₃H₇ | H | F | Cl | 1.4451 |
| 22 | C₂H₅O | n-C₃H₇ | H | F | F | 1.4271 |
| 23 | (chlorotrifluorocyclobutyloxy) | n-C₃H₇ | H | F | Cl | 1.4464 |
| 24 | C₂H₅ | n-C₃H₇ | H | F | Cl | |
| 25 | C₂H₅ | t-C₄H₉ | H | F | Cl | |
| 26 | CH₃ | n-C₃H₇ | H | F | Cl | |
| 27 | n-C₃H₇ | n-C₃H₇ | H | F | Cl | |
| 28 | C₂H₅ | n-C₃H₇ | H | F | F | |
| 29 | CH₃O | n-C₃H₇ | H | F | F | |
| 30 | n-C₃H₇ | n-C₃H₇ | H | F | F | |
| 31 | C₂H₅O | CH₂C≡CH | H | F | F | |
| 32 | C₂H₅O | CHC≡CH / CH₃ | H | F | F | |
| 33 | C₂H₅O | CH₂CH=CH₂ | H | F | F | |
| 34 | C₂H₅O | CH₂CH(CH₃)₂ | H | F | F | |
| 35 | C₂H₅O | C₂H₅ | H | F | F | |
| 36 | C₂H₅O | CH₂—C≡CH | H | F | Cl | |
| 37 | C₂H₅O | CH(CH₃)C≡CH | H | F | Cl | |
| 38 | C₂H₅O | CH₂—CH=CH₂ | H | F | Cl | |
| 39 | C₂H₅O | CH₂CH(CH₃)₂ | H | F | Cl | |
| 40 | C₂H₅O | C₂H₅ | H | F | Cl | |
| 41 | C₂H₅O | CH₂CH₂OCH₃ | H | F | Cl | |
| 42 | C₂H₅O | CH₂CH₂OCH₃ | H | F | F | |
| 43 | C₂H₅O | n-C₄H₉ | H | F | F | |
| 44 | C₂H₅O | n-C₄H₉ | H | F | Cl | |
| (X = S) | | | | | | |
| 45 | C₂H₅ | n-C₃H₇ | H | F | Cl | |
| 46 | C₂H₅ | sec-C₄H₉ | H | F | Cl | 1.4954 |
| 47 | C₂H₅ | n-C₃H₇ | H | F | Cl | |
| 48 | C₂H₅ | t-C₄H₉ | H | F | Cl | 1.4960 |
| 49 | CH₃ | n-C₃H₇ | H | F | Cl | |
| 50 | CH₃ | n-C₃H₇ | H | F | F | |
| 51 | C₂H₅ | n-C₃H₇ | H | F | F | |

-continued

Compounds of the formula Ia

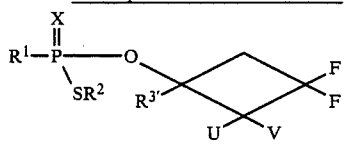

(Ia)

| Example No. | R¹ | R² | R³' | U | V | Physical data ($n_D^{20}$) |
|---|---|---|---|---|---|---|
| 52 | $C_2H_5$ | sec-$C_4H_9$ | H | F | F | |
| 53 | n-$C_3H_7$ | n-$C_3H_7$ | H | F | F | |
| 54 | $CH_3O$ | n-$C_3H_7$ | H | F | Cl | |
| 55 | $CH_3O$ | n-$C_3H_7$ | H | F | F | |
| 56 | $C_2H_5O$ | n-$C_3H_7$ | H | F | F | 1.4721 |
| 57 | $C_2H_5O$ | t-$C_4H_9$ | H | F | Cl | |
| 58 | $C_2H_5O$ | sec-$C_4H_9$ | H | F | F | 1.4642 |
| 59 | $C_2H_5O$ | sec-$C_4H_9$ | H | F | Cl | 1.4825 |
| 60 | $C_2H_5O$ | n-$C_3H_7$ | H | F | Cl | 1.4825 |
| 61 | $C_2H_5O$ | n-$C_4H_9$ | H | F | Cl | |
| 62 | $C_2H_5O$ | n-$C_4H_9$ | H | F | F | |
| 63 | $C_2H_5O$ | $CH_2-C\equiv CH$ | H | F | Cl | |
| 64 | $C_2H_5O$ | $CH(CH_3)C\equiv CH$ | H | F | Cl | |
| 65 | $C_2H_5O$ | $CH_2-CH=CH_2$ | H | F | Cl | |
| 66 | $C_2H_5O$ | $CH_2CH(CH_3)_2$ | H | F | Cl | |
| 67 | $C_2H_5O$ | $C_2H_5$ | H | F | Cl | |
| 68 | $C_2H_5O$ | $CH_2CH_2OCH_3$ | H | F | Cl | |
| 69 | $C_2H_5O$ | $CH_2CH_2OCH_3$ | H | F | F | |
| 70 | $C_2H_5O$ | n-$C_4H_9$ | H | F | F | |
| 71 | $C_2H_5O$ | n-$C_4H_9$ | H | F | Cl | |

PREPARATION OF THE PRECURSORS

Example A1

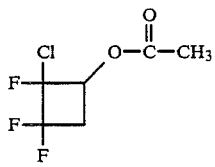

1,120 g (13 mol) of vinyl acetate are reacted with 400 g (3.43 mol) of trifluorochloroethylene in the presence of 8 g of hydroquinone and 24 drops of dipentene in a 3 l enamelled autoclave. The reaction temperature is 220° C. for a reaction time of 3 hours. The reaction mixture is purified by distillation in a thin film evaporator.

Yield: 526 g (75% of theory).
B.p.$_{44}$ mbar=73°–85° C.
$n_D^{20}$=1.3972.
¹H NMR $\delta$=2.1–3.1 ppm. 3.9 ppm. 4.2–4.7 ppm.

Example A2

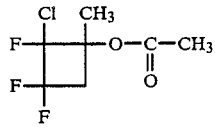

500 g (5.0 mol) of isopropylene acetate are set, in a 1.3 enamelled autoclave and in the presence of 4 g of hydroquinone and 10 drops of dipentene, with 155 g (1.33 mol) of trifluorochloroethylene for 3 hours at 220° C. The reaction mixture is purified by distillation.

Yield: =62 g (22% of theory).
B.p.$^{24}$ mbar=65° C.
$n_D^{20}$=1.402
¹H NMR $\delta$=1.8 ppm (3). 2.1 ppm (3). 2.7–3.1 ppm (2).

Example A3

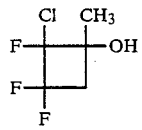

62 g (0.27 mol) of trifluorochloromethylcyclobutyl acetate according to Example A2 are added, at 25° C., to 32 g (0.64 mol) of hydrazine hydrate in 200 ml of diethyl ether, and the reaction mixture is stirred for a further 16 hours at 20° C. Purification is effected by distillation.

Yield: 58 g.
B.p.$_{18}$ mbar=50° C.
$n_D^{20}$=1.402.
¹H NMR $\delta$=1.5 ppm (3). 2.5–2.8 ppm (3).

Example A4

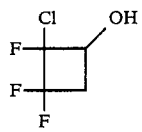

450 g (2.2 mol) of trifluorochlorocyclobutyl acetate according to Example A1 are added, at 0° C., to 120 g (2.4 mol) of hydrazine hydrate in 80.0 ml of diethyl ether. The reaction mixture is stirred for a further 14 hours at 20° C. The ether phase is separated off and dried over $Na_2SO_4$. The product is purified by distillation.

Yield: 344 g (98% of theory).
B.p.$_{70}$ mbar=70° C.
$n_D^{20}$=1.3965.
¹H NMR=2.2–3.1 ppm (2). 3.8 ppm (1). 4.4 ppm (1).
The other compounds of the formulae (III) or (XII) can be prepared analogously. 2,2,3,3-Tetrafluorocyclobutanol has been described previously (W. D. Philipps, J. Chem. Phys. 25, 949 (1956).

The biological action of the compounds according to the invention will be illustrated by means of the following examples.

Example A

Test insect: *Diabrotica balteata*—larvae in the soil
Solvent: 3 parts by weight of acetone
Emulsifier: 1 part by weight of alkylaryl polyglycol ether An appropriate formulation of active compound is prepared by mixing 1 part by weight of active compound with the indicated amount of solvent, adding the indicated amount of emulsifier and diluting the concentrate with water to the desired concentration.

The formulation of active compound is intimately mixed with the soil. In this connection the concentration of the active compound in the formulation is of virtually no importance; the only factor appropriate is the amount by weight of active compound per volume unit of soil, which is quoted in ppm (mg/l). The soil is filled into 0.5 pots and these are allowed to stand at 20° C.

Immediately after the soil has been made up, 6 pregerminated corn kernels are placed in each pot. After 2 days, the appropriate test insects are put into the treated soil. After a further 7 days, the % efficiency of the active compound is determined by counting the dead and living test insects. The efficiency is 100% if all the test insects have been destroyed; it is 0% if there are exactly as many live test insects as in the untreated control.

The compounds of Preparation Examples 1, 4 and 10, for example, exhibited an efficiency of 100% in this test at a concentration of, for example, 2.3 ppm.

Example A1

Test insect: *Phorbia antiqua* maggots (in the soil)
Solvent: 3 parts by weight of acetone
Emulsifier: 1 part by weight of alkylaryl polyglycol ether An appropriate formulation of active compound is prepared by mixing 1 part by weight of active compound with the indicated amount of solvent, adding the indicated amount of emulsifier and diluting the concentrate with water to the desired concentration.

The formulation of active compound is intimately mixed with the soil. In this connection the concentration of the active compound in the formulation is of virtually no importance; the only decisive factor is the amount by weight of active compound per volume unit of soil, which is quoted in ppm (mg/l). The soil is filled into pots and the latter are allowed to stand at room temperature.

After 24 hours, the test insects are put into the treated soil and, after a further 2 to 7 days, the % efficiency of the active compound is determined by counting the dead and living test insects. The efficiency is 100% if all the test insects have been destroyed; it is 0% if there are exactly as many live test insects as in the untreated control.

The compounds of Preparation Examples 1, 2, 4, 5, 6, 10, 23 and 45, for example, exhibited an efficiency of 100% in this test at an active compound concentration of, for example, 10 ppm.

Example B

Test insect: *Phaedon cochleariae* larvae
Solvent: 3 parts by weight of acetone
Emulsifier: 1 part by weight of alkylaryl polyglycol ether A suitable formulation of active compound is prepared by mixing 1 part by weight of active compound with the indicated amount of solvent, adding the indicated amount of emulsifier and diluting the concentrate with water to the desired concentration.

The formulation of active compound is intimately mixed with soil. In this connection the concentration of the active compound in the formulation is of virtually no importance; the decisive factor is only the amount by weight of active compound per volume unit of soil, which is quoted in ppm (=mg/l). The treated soil is filled into pots and the latter are planted with cabbage (*Brassica oleracea*). The active compound can thus be absorbed from the soil by the plant roots and transported into the leaves.

For the detection of the root-systemic effect, the leaves alone are populated with the abovementioned test insects after 7 days. Evaluation by counting or estimating the dead insects is carried out after a further 2 days. The root-systemic action of the active compound is derived from the mortality figures. It is 100% if all the test insects have been destroyed, and 0% if there are exactly as many live test insects as in the case of the untreated control.

The compounds of Preparation Examples 1 and 10, for example, exhibited a mortality figure of 100% in this test at a concentration of, for example, 20 ppm.

Example C

Test insect: *Myzus persicae*
Solvent: 3 parts by weight of acetone
Emulsifier: 1 part by weight of alkylaryl polyglycol ether A suitable formulation of active compound is prepared by mixing 1 part by weight of active compound with the indicated amount of solvent, adding the indicated amount of emulsifier and diluting the concentrate with water to the desired concentration.

The formulation of active compound is intimately mixed with soil. In this connection the concentration of the active compound in the formulation is of virtually no importance; the decisive factor is only the amount by weight of active compound per volume unit of soil, which is quoted in ppm (=mg/l). The treated soil is filled into pots and the latter are planted with cabbage (*Brassica oleracea*). The active compound can thus be absorbed from the soil by the plant roots and transported into the leaves.

For the detection of the root-systemic effect, the leaves alone are populated with the abovementioned test insects after 7 days. Evaluation by counting or estimating the dead insects is carried out after a further 2 days. The root-systemic action of the active compound is derived from the mortality figures. It is 100% if all the test insects have been destroyed, and 0% if there are exactly as many live test insects as in the case of the untreated control.

The compounds of Preparation Examples 1 and 10, for example, exhibited a mortality figure of 100% in this test at a concentration of, for example, 20 ppm.

Example D

Test nematode: *Meloidogyne incognita*
Solvent: 3 parts by weight of acetone
Emulsifier: 1 part by weight of alkylaryl polyglycol ether A suitable formulation of active compound is prepared by mixing 1 part by weight of active compound with the indicated amount of solvent, adding the indicated amount of emulsifier and diluting the concentrate with water to the desired concentration.

The formulation of active compound is intimately mixed with soil heavily infested with the test nematodes. In this connection the concentration of the active compound in the formulation is of virtually no importance; the decisive factor is only the amount of active compound per volume unit of soil, which is quoted in ppm. The treated soil is filled into pots, lettuce is sown therein and the pots are kept at a greenhouse temperature of 27° C.

After four weeks the lettuce roots are examined for attack by nematodes (root galls), and the % efficiency of the active compound is determined. The efficiency is 100% if the attack is completely prevented; it is 0% if the attack is exactly as great as in the case of the control plants in untreated, but similarly infested, soil.

The compounds of Preparation Examples 1, 4, 5, 6 and 10, for example, exhibited an efficiency of 100% in this test at a concentration of, for example, 10 ppm.

Example E

Test nematode: *Globodera rostochiensis*
Solvent: 3 parts by weight of acetone
Emulsifier: 1 part by weight of alkylaryl polyglycol ether A suitable formulation of active compound is prepared by mixing 1 part by weight of active compound with the indicated amount of solvent, adding the indicated amount of emulsifier and diluting the concentrate with water to the desired concentration.

The formulation of active compound is intimately mixed with soil heavily infested with the test nematodes. In this connection the concentration of the active compound in the formulation is of virtually no importance, the decisive factor is only the amount of active compound per volume unit of soil, which is quoted in ppm. The treated soil is filled into pots, potatoes are planted therein, and the pots are kept at a greenhouse temperature of 18° C.

After six weeks the potato roots are examined for cysts, and the % efficiency of the active compound is determined. The efficiency is 100% if the attack is completely prevented; it is 0% if the attack is exactly as great as in the case of the control plants in untreated, but similarly infested, soil.

The compounds of Preparation Examples 1, 4, 5, 6 and 10, for example, exhibited an efficiency of 100% in this test at a concentration of, for example, 10 ppm.

Example F

Aphis test (systemic action)
Solvent: 3 parts by weight of acetone
Emulsifier: 1 part by weight of alkylaryl polyglycol ether A suitable formulation of active compound is prepared by mixing 1 part by weight of active compound with the indicated amount of solvent and the indicated amount of emulsifier and diluting the concentrate with water to the desired concentration.

Bean plants (*Vicia fabae* which have been severely attacked by the black bean aphid (*Aphis fabae*) are watered with 20 ml each of active compound formulation in such a way that the active compound formulation penetrates into the soil without wetting the shoot. The active compound is absorbed by the roots and transmitted into the shoot.

The % mortality is determined after the desired period. In this connection 100% means that all the aphids have been destroyed; 0% means that no aphids have been destroyed.

The compound of Preparation Example 1, for example, exhibited a mortality of 100% after 4 days in this test at a concentration of, for example, 0.1%.

Example G $LT_{100}$ test for diptera
Test insects: *Musca domestica*, resistant
Number of test insects: 25
Solvent: Acetone 2 parts by weight of active compound are taken in 1,000 parts by volume of solvent. The solution thus obtained is diluted with further solvent to the desired lower concentrations.

2.5 ml of active compound solution are pipetted into a petri dish. On the base of the petri dish there is a filter paper with a diameter of about 9.5 cm. The petri dish is left open until the solvent has completely evaporated. The amount of active compound per $m^2$ of filter paper varies according to the concentration of the solution of active compound. A number of test insects is then put into the petri dish and the latter is covered with a glass lid.

The condition of the test insects is monitored continuously. The time required for a 100% knockdown effect (LT100) is determined.

The compound of Preparation Example 1, for example, exhibited an $LT_{100}$ value of 100 minutes in this test at a concentration of, for example, 0.1%.

Example H

Test insects: *Blattella germanica*
Solvent: Acetone 2 parts of active compound are taken up in 1,000 parts by volume of solvent. The solution thus obtained is diluted with further solvent to the desired concentrations.

2.5 ml of active compound solution are pipetted into a petri dish. On the base of the petri dish there is a filter paper with a diameter of about 9.5 cm. The petri dish is left open until the solvent has completely evaporated. The amount of active compound per $m^2$ of filter paper varies according to the concentration of the solution of active compound. A number of test insects is then put into the petri dish and the latter is covered with a glass lid.

The condition of the test insects is monitored 3 days after the preparation of the test. The % mortality is determined. In this connection 100% means that all the test insects have been destroyed; 0% means that no test insects have been destroyed.

The compound of Preparation Example 1, for example, exhibited a mortality of 100% in this test at a concentration of, for example, 0.1%.

It is understood that the specification and examples are illustrative but not limitative of the present inven-

We claim:

1. An O-(halogenocyclobutyl) S-(alkyl) (di)thiophosph(on)ate of the formula

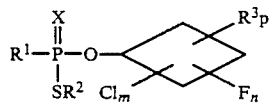

in which x represents oxygen or sulphur,
p-represents zero, one or two,
m represents zero, one or two,
n represents 2, 3 or 4,
$R^1$ represents $(C_1-C_6)$-alkyl, $(C_1-C_6)$-alkoxy, $(C_1-C_6)$-alkenyloxy, $(C_1-C_6)$-alkinyloxy, (2-hexahydropyranyl)methoxy, (2-tetrahydrofuranyl)methoxy, $(C_1-C_6)$-alkoxy-$(C_1-C_4)$-alkoxy, $(C_1-C_6)$-alkylthio-$C_1-C_4$)-alkoxy or 3,3,2-trifluoro-2-chlorocyclobutoxy,
$R^2$ represents $(C_1-C_6)$-alkyl, $(C_2-C_6)$-alkenyl, $(C_2-C_6)$-alkinyl, (2-hexahydropyranyl)methyl, (2-tetrahydrofuranyl)methyl, $(C_1-C_6)$-alkylthio-$(C_1-C_4)$-alkyl or $(C_1-C_6)$-alkoxy-$(C_1-C_4)$-alkyl,
and $R^{3'}$ represents hydrogen or $(C_1-C_4)$-alkyl.

2. An O-halogenocyclobutyl S-alkyl (di)thiophosphon(on)ate according to claim 1, of the formula

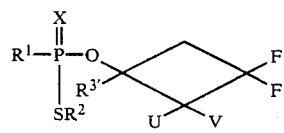

(Ia)

in which

X represents oxygen or sulphur,
U represents hydrogen, fluorine or chlorine and
V represents hydrogen, fluorine or chlorine.

3. An O-halogenocyclobutyl S-alkyl (di)thiophosph(on)ate according to claim 2, in which $R^1$ represents $(C_1-C_4)$-alkyl, $(C_1-C_4)$-alkoxy, $(C_2-C_4)$-alkenyloxy, $(C_2-C_4)$-alkinyloxy, (2-tetrahydropyranyl)methoxy, $(C_1-C_4)$-alkoxy-$(C_1-C_4)$-alkoxy or $(C_1-C_4)$-alkylthio-$(C_1-C_4)$-alkoxy,
$R^2$ represents $(C_1-C_4)$-alkyl, $(C_2-C_4)$-alkenyl, $(C_2-C_4)$-alkinyl, (2-tetrahydrofuranyl)methyl, $(C_1-C_4)$-alkoxy-$(C_1-C_4)$-alkyl or $(C_1-C_4)$-alkylthio$(C_1-C_4)$-alkyl,
$R^{3'}$ represents hydrogen or methyl,
X represents oxygen or sulphur,
U represents hydrogen, fluorine or chlorine and
V represents hydrogen, fluorine or chlorine.

4. A compound according to claim 1, wherein such compound is S-propyl O-ethyl O-(3,3,2-trifluoro-2-chlorocyclobutyl) thiophosphate of the formula

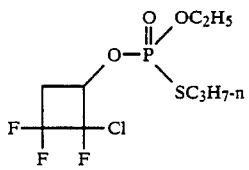

5. A compound according to claim 1, wherein such compound is S-sec.butyl O-(3,3,2-trifluoro-2-chlorocyclobutyl) ethanethiophosphonate of the formula

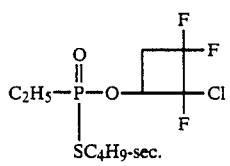

6. A compound according to claim 1, wherein such compound is S-sec. butyl O-ethyl O-(3,3,2-trifluoro-2-chloro-1-methyl-cyclobutyl) thiophosphate of the formula

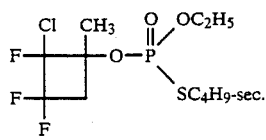

7. A compound according to claim 1, wherein such compound is S-propyl O-ethyl O-(3,3,2-trifluoro-2-chloro-1-methyl-cyclobutyl) thiophosphate of the formula

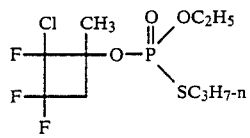

8. A compound according to claim 1, wherein such compound is S-methyl O-ethyl O-(3,3,2-trifluoro-2-chlorocyclobutyl) thiophosphate of the formula

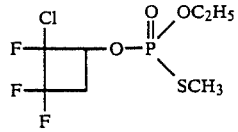

9. An insecticidal, acaricidal or nematicidal composition comprising an insecticidally, acaricidally or nematicidally effective amount of a compound according to claim 1 and a diluent.

10. A method of combating insects acarids or nematodes which comprises applying to such insects, acarids or nematodes an insecticidally, acaricidally or nematicidally effective amount of a compound according to claim 1.

11. The method according to claim 10, wherein such compound is
S-propyl O-ethyl O-(3,3,2-trifluoro-2-chlorocyclobutyl) thiophosphate, S-sec.butyl O-(3,3,2-trifluoro-2-chlorocyclobutyl) ethanethiophosphonate, S-sec.butyl O-ethyl O-(3,3,2-trifluoro-2-chloro-1-methyl-cyclobutyl thiophosphate, S-propyl O-ethyl O-(3,3,2-trifluoro-2-chloro-1-metyl-cyclobutyl) thiophosphate, S-sec. butyl O-ethyl O-(3-chloro-3-fluorocyclobutyl) thiophosphate, S-methyl O-ethyl O-(3,3,2-trifluoro-2-chlorocyclobutyl) thiophosphate, or S-n-propyl O-ethyl O-(3-chloro-3-fluorocyclobutyl) thiophosphate.

12. A compound according to claim 1, wherein such compound is S-sec.butyl O-ethyl O-(3-chloro-3-fluorocyclobutyl) thiophosphate of the formula

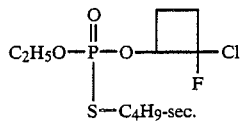

13. A compound according to claim 1, wherein such compound is S-n-propyl O-ethyl O-(3-chloro-3-fluorocyclobutyl) thiophosphate of the formula

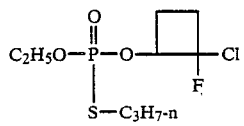

* * * * *

UNITED STATES PATENT AND TRADEMARK OFFICE
CERTIFICATE OF CORRECTION

PATENT NO. : 4,973,583

DATED : November 27, 1990

INVENTOR(S) : Kruger et al.

It is certified that error appears in the above-identified patent and that said Letters Patent is hereby corrected as shown below:

Title Page      [54] Title: 2nd line delete " THIPHOSPH) " and substitute -- THIOPHOSPH --

Col. 1, line 2    2nd line of Title delete " THIPHOSPH) " and substitute -- THIOPHOSPH --

Signed and Sealed this

Eighth Day of December, 1992

*Attest:*

DOUGLAS B. COMER

*Attesting Officer*    *Acting Commissioner of Patents and Trademarks*